US006566349B1

(12) United States Patent
Anderson et al.

(10) Patent No.: US 6,566,349 B1
(45) Date of Patent: May 20, 2003

(54) SAFER ORGANOPHOSPHOROUS COMPOSITIONS

(75) Inventors: Thomas E. Anderson, Myersville, MD (US); William M. Fletcher, Bahama, NC (US); Hector E. Portillo, Greenville, MS (US)

(73) Assignee: BASF Corporation, Mt. Olive, NJ (US)

( * ) Notice: Subject to any disclaimer, the term of this patent is extended or adjusted under 35 U.S.C. 154(b) by 150 days.

(21) Appl. No.: 09/649,422

(22) Filed: Aug. 28, 2000

(51) Int. Cl.[7] .......................... A61K 31/66; A01N 57/00
(52) U.S. Cl. ........................................................ 514/75
(58) Field of Search ............................................. 514/75

(56) References Cited

U.S. PATENT DOCUMENTS

| | | | |
|---|---|---|---|
| 4,834,908 A | 5/1989 | Hazen et al. ................ 252/356 |
| 4,904,464 A | * 2/1990 | Albanese ..................... 424/45 |
| 4,904,695 A | 2/1990 | Bell ............................ 514/521 |
| 4,966,728 A | 10/1990 | Hazen et al. ................ 252/354 |
| 4,994,261 A | 2/1991 | Scher et al. .................. 424/10 |
| 5,078,782 A | 1/1992 | Nielsen et al. ................ 71/100 |
| 5,084,087 A | 1/1992 | Hazen et al. .................. 71/123 |
| 5,102,442 A | 4/1992 | Hazen et al. ................... 71/91 |
| 5,108,488 A | 4/1992 | Etheridge ....................... 71/98 |
| 5,238,604 A | 8/1993 | Hazen et al. ............... 252/356 |
| 5,326,560 A | 7/1994 | Henderson et al. ........... 424/93 |
| 5,399,542 A | 3/1995 | Hamilton et al. ........... 504/224 |
| 5,444,078 A | 8/1995 | Yu et al. ..................... 514/372 |
| 5,580,567 A | 12/1996 | Roberts ...................... 424/405 |
| 5,612,048 A | 3/1997 | Synek | |
| 5,741,502 A | 4/1998 | Roberts ...................... 424/405 |

FOREIGN PATENT DOCUMENTS

| | | |
|---|---|---|
| JP | 58-172304 | 10/1983 |
| JP | 9-268108 A | 10/1997 |
| WO | WO 92/06596 | 4/1992 |
| WO | 97/11606 | 4/1997 |
| WO | 9929171 | * 6/1999 |

* cited by examiner

Primary Examiner—Alton Pryor

(57) ABSTRACT

The efficacy of insecticidal compositions (especially organophosphate insecticides) is enhanced through the blending of the insecticide with fatty acid containing crop oil concentrate.

12 Claims, No Drawings

SAFER ORGANOPHOSPHOROUS COMPOSITIONS

FIELD OF THE INVENTION

The present invention relates generally to insecticidal compositions. More specifically, the present invention relates to insecticidal compositions with increased efficacy and/or insecticidal compositions that are safened.

BACKGROUND OF THE INVENTION

Pesticides, especially organophosphate insecticides, have come under increased scrutiny. Specifically, the Food Quality Protection Act of 1996 (FQPA) mandates that the EPA reassess all pesticide tolerances and exemptions from tolerances by 2006. Many insecticides have been assigned top priority for tolerance reassessment and risk assessment. However, the fact remains that chemical pesticides are useful for protecting economically important crops. Thus, there is a need for insecticidal compositions which are more efficacious or which retain their efficacy at lower doses.

As discussed in U.S. Pat. No. 5,326,560 to Henderson, the art has attempted to manage the problem of insecticide toxicity in the environment through careful selection and application of herbicides and pesticides. As described therein, ideal application of insecticides to crops might involve applying minimal quantities of insecticides which maintain effectiveness over a longer period of time. Many insecticides currently available, such as pyrethrum, the pyrethroids, organophosphates, and biologicals, rapidly degrade after exposure to ultraviolet radiation and/or through hydrolysis and oxidation. Unfortunately, these active ingredients may degrade well before they have accomplished their purpose. To address these problems, Henderson discloses an insecticide carrier that is a mixture of petrolatum (preferably white petroleum), diatomaceous earth, and preferably a diluent, such as "crop oil." The carrier is reported to provide increased wash-off resistance, increased effectiveness against insects, adhesion to vegetation and ultraviolet shielding. The crop oil is an inert petroleum agricultural spray oil which may be a light to heavy paraffin oil, having viscosity ranging from 40 to 85 sec. Saybolt at 4° C. The disclosed crop oils are reported to be non-phytotoxic. Examples of diluent crop oils include CHEVRON BASE OIL C® and SUN 11N®. Henderson reports that low rates of the insecticidal toxicant (a bacterial insecticide) are more effective when used in combination with the proper carrier/adjuvant. It should be considered, however, that increased persistence of pesticidal residues may not be advantageous in all cases because, for example, they might be ingested by the consumer of the produce.

JP 58-172304, assigned to Japan Agricultural Chemicals discloses an ant control agent comprising organophosphorus insecticides plus anionic and nonionic surfactants which is applied to wood surfaces. The anionic surfactant is preferably dodecylbenzene calcium sulfonate. The non-ionic surfactant is polyoxyethylene alkylphenol-ether. The ant control agent reportedly permeates the wood and adheres to the wood surface better than the prior art materials.

WO 97/11606, assigned to BASF AG discloses a means for combating parasitic fungi. The means involves using as active agents fenazaquin and at least one compound that prevents respiration in the cytochrome III complex. These agents can be blended with a variety of carriers including aromatics, paraffins, ketones, amines, kaolins, silicates, non-ionic and anionic surfactants.

JP 9-268108A assigned to Hokko Chemical, discloses a low dose organophosphorus compound (e.g., acephate), non-ionic and/or anionic surfactants and a solid carrier having a specified degree of whiteness. The non-ionic surfactants can be polyoxyethylene alkyl ether, polyoxyethylene fatty acid ester, polyoxyethylene aryl phenyl ether, polyoxyethylene alkyl phenyl ether, polyoxyethylene sorbitan fatty acid ester, polyoxyethylene polyoxypropylene block polymer, or the like, having an HLB in the range of the 13 to 18. The anionic surfactants may be higher alcohol sulfuric acid ester salt, higher alkyl ether sulfuric acid ester salt, sulfonation fatty acid ester, sulfonation olefin, polyoxyethylene alkyl ether sulfuric acid ester salt, polyoxyethylene alkyl phenyl ether sulfuric acid ester salt, polyoxyethylene styrene-modified phenyl ether sulfuric acid ester salt, polyoxyethylene polyoxypropylene block polymer sulfuric acid ester salt, polyoxyethylene alkyl phenyl ether sulfonate, polyoxyethylene alkyl phenyl ether acetic acid ester sulfonate, polyoxyalkylene alkyl phenyl ether acetic acid ester sulfonate, polyoxyalkylene aryl phenyl ether acetic acid ester sulfonate, alkylbenzene sulfonate, alkyl naphthalene sulfonate, dialkyl sulfosuccinic acid salt, lignin sulfonate, higher alcohol phosphoric acid ester salt, higher alkyl ether phosphoric acid ester salt, polyoxyethylene alkyl ether phosphoric acid ester salt, polyoxyethylene alkyl phenyl ether phosphoric acid ester salt, polyoxyethylene styrenated phenyl ether phosphoric acid ester salt, the polyoxyalkylene styrene-modified phenyl ether phosphoric acid ester salt, polyoxyethylene polyoxypropylene block polymer phosphoric acid ester salt, naphthalene sulfonic acid formalin condensate, or the like. The working examples in JP 9-268108A teach the use of non-ionic or anionic surfactants. Both types of surfactants in one formulation are not taught.

At col. 8, lines 45–47, U.S. Pat. No. 5,108,488 to Etheridge teaches that when the herbicidal composition described therein is to be used as a pre-emergent treatment for weed control. A fertilizer, an insecticide, a fungicide, or another herbicide may be included in the formulation.

U.S. Pat. No. 5,399,542 to Hamilton, et al. is also directed to herbicidal compositions which may further contain an adjuvant, including a mixture of petroleum hydrocarbons, alkyl esters and acids, anionic surfactants and inert materials, e.g., DASH® adjuvant available from BASF Corporation.

U.S. Pat. Nos. 4,966,728 and 5,084,087, both to Hazen et. al., describe adjuvants that are useful for herbicide formulations.

Definitions and Usage of Terms

The term "necessary effective dose", as used herein, means the dose at which a desired pesticidal activity is achieved.

The term "effective", as used herein, means the typical amount, dosage or concentration or percentage of an active ingredient necessary to achieve a desired result.

The term "carrier", as used herein, means an inert material added to a technical toxicant to facilitate later dilution to field strength.

The term "diluent", as used herein, means a material, liquid or solid, serving to dilute the technical toxicant to field strength for adequate plant coverage, maximum effectiveness and economy.

Organophosphorus compounds, such as organophosphates, are anticholinesterase chemicals which damage or destroy cholinesterase, the enzyme required for nerve function in the living body. Various alkoxy groups (X) are often attached to the phosphorus as follows:

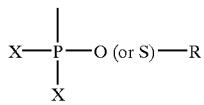

The term "HLB", as used herein, means hydrophilic/lipophilic balance. For example, emulsifiers typically involve a molecule that combines hydrophilic and lipophilic groups. The hydrophilic/lipophilic balance (HLB) is a major factor in determining the emulsification characteristics of a non-ionic surfactant. Surfactants with lower HLB values are more lipophilic, while surfactants with higher HLB values are more hydrophilic. These HLB values assist formulators by reducing the number of surfactants to be evaluated for a given application. In general, surfactant function falls within specific HLB ranges, noted below:

| HLB | Surfactant Function |
|---|---|
| 4–6 | Water/oil emulsifier |
| 7–9 | Wetting agent |
| 8–18 | Oil/water emulsifier |
| 13–15 | Detergent |
| 10–18 | Solubilizer |

In the present application, all percentages are weight percent unless otherwise indicated.

SUMMARY OF THE INVENTION

It is an object of the present invention to provide more efficacious organophosphorus insecticidal compositions.

Another object of the present invention is to provide organophosphorus insecticidal compositions that demonstrate substantially equivalent efficacy at reduced application rates.

In accordance with these objects, it has been surprisingly discovered that blending an organophosphorus insecticidal composition with a certain class of adjuvant enables the use of lower levels of said insecticide while maintaining the active ingredient's effectiveness. Also, such blending improves the efficacy of certain organophosphorus insecticides at equivalent application rates.

Thus, in one embodiment the present invention is an insecticidal composition composed of from about 0.015% to about 3.6% of one or more organophosphate insecticidal compound; from about 0.5% to about 99.5% of an adjuvant composition comprising, based on the weight of the adjuvant:
  (a) from about 20 to about 90 weight percent of a lower alkanol ester of a fatty acid containing from 4–22 carbon atoms;
  (b) from about 4 to about 40 weight percent of an anionic surfactant selected from the group consisting of partial sulfate and phosphate esters and carboxylates of monohydroxylfunctional polyoxyalkylene ethers;
  (c) from about 2 to about 20 weight percent of a long chain carboxylic acid containing from about 10 to about 20 carbon atoms; and
  (d) optionally, a hydrocarbon;
and diluent.

In another embodiment, the insecticidal composition is composed of about 0.5%–about 99.5% of an adjuvant composition comprising, based on the weight of the adjuvant:
  (a) from about 30 to about 80 percent of a lower alkanol ester of a fatty acid containing from 10 to about 20 carbon atoms;
  (b) from about 4 to about 20 percent of an anionic surfactant selected from the group consisting of the partial sulfate and phosphate esters and carboxylates of monohydroxyl-functional polyoxyalkylene ethers having an average molecular weight of from 600 to about 1200 Daltons; and
  (c) from 4 to about 6 percent of a long chain carboxylic acid having from 10 to about 20 carbon atoms;
about 0.015% to about 3.6% of one or more organophosphate insecticidal compound; and diluent.

Another embodiment of the present invention is an insecticidal composition composed of about 0.5%–about 99.5% of an adjuvant composition comprising, based on the weight of the adjuvant:
  (a) from about 2 to about 30 percent of an anionic surfactant selected from the group consisting of the partial sulfate and phosphate esters and carboxylates of monohydroxyl-functional polyoxyalkylene ethers and their alkali metal, alkaline earth metal and ammonium salts;
  (b) one of the following fatty acid components:
    (i) from 1 to about 20 percent of a fatty acid having from 10 to about 22 carbon atoms; and
    (ii) from 10 to about 96 percent of a lower alkanol ester of a fatty acid having form 10 to about 22 carbon atoms; and
  (c) a hydrocarbon component with is
    (i) from 90 to about 10 percent when the fatty acid component is (b) (i); and
    (ii) up to about 70 percent when the fatty acid component is (b) (ii); about 0.015%–about 3.6% of one or more organophospate insecticidal compounds; and diluent.

Another aspect of the present invention is a method for controlling insect populations in crops. The method involves applying to said crop an effective amount of one of the insecticidal compositions described above. It is method is especially efficacious when used to control insect populations or the lepidopteran order.

DETAILED DESCRIPTION OF THE PREFERRED EMBODIMENTS

To promote an understanding of the principles of the present invention, descriptions of specific embodiments of the invention follow and specific language is used to describe them. It will nevertheless be understood that no limitation of the scope of the invention is intended by the use of specific language. Alterations, further modifications and such further applications of the principles of the invention discussed are contemplated as would normally occur to one ordinarily skilled in the art to which the invention pertains.

As discussed, the present invention relates to organophosphorus insecticidal composition containing an organophosphorus insecticide, an adjuvant and, optionally, a diluent.

The Insecticidal Compounds Useful in the Present Invention

The preferred organophosphorus compounds useful in the practice of the present invention are represented by the following structures:

Phosphate (e.g. dicrotophos):

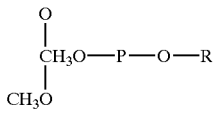

Phosphorothioate (e.g. parathion):

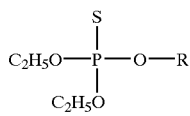

Phosphorothioate (e.g. cyanothorate):

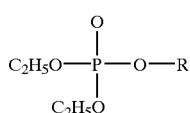

Phosphorothioate (e.g. phorate):

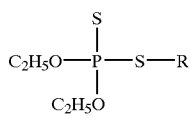

Phosphonate(e.g. trichlorfon):

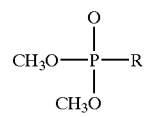

Phosphoramidate (e.g. crufomate):

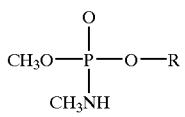

Specific organophosphorus compounds useful in the practice of the present invention include, but are not limited to, O,S-dimethyl acetylphosphoramidothioate, CAS Number 30560-19-1 (Acephate); S-[2-(formylmethylamino)-2-oxoethyl]O,O-dimethyl phosphorodithioate, CAS Number 2540-82-1 (Formothion); S-6-chloro-2,3-dihydro-2-oxo-oxazolo[4,5-b]pyridin-3-ylmethyl]O,O-dimethyl phosphorothioate (IUPAC), CAS Number 35575-96-3 (Azamethiphos); O,O-diethyl S-[4-oxo-1,2,3-benzotriazin-3(4H)-yl)-methyl]phosphorodithioate, CAS Number 2642-71-9 (Azinphos-ethyl); O,O-dimethyl S-[4-oxo,1,2,3-benzotriazin-3(4H)-yl)methyl]-phosphorodithioate (CAS 9CI), CAS Number 86-50-0 (Azinphos-methyl); 2-chloro-1-(2,4-dichlorophenyl)vinyl diethylphosphate (IUPAC), CAS Number 470-90-6 (Chlorfenvinphos); O-4-cyanophenyl O,O-dimethyl phosphorothioate, CAS Number 2636-26-2 (Cyanophos); S-[(4-chlorophenyl)thio]methyl O,O-diethyl phosporothioate (IUPAC), CAS Number 786-19-6 (Danifos); O,O-diethyl O-[4-methylsulfinyl)phenyl] phosphorothioate (CAS), CAS Number 115-:90-2, (Fensulfothion); S,S,S-tributyl phosphorotrithioate (IUPAC), CAS Number 78-48-8 (Tribufos); O,O-diethyl O-[6-methyl-2(1-methylethyl)-4-pyrimidinyl] phosphorothioate (CAS 9CI); O,O-diethyl O-(2isopropyl-6-methyl-4-pyrimidinyl)phosphorothioate (CAS 8CI), CAS Number 333-41-5 (Active ingredient of Diazinon); O,O-dimethyl S-methylcarbamoylmethyl phosphorodithioate, CAS Number 60-51-5 (Dimethoate); S,S'-(1,4-dioxane-2,3-diyl)O,O,O',O-tetraethyl bis(phosphorodithioate) (IUPAC), CAS Number 78-34-2 (Dioxathion); O,O-diethyl S-[2-(ethylthio)ethyl]phosphorodithioate (CAS), CAS Number 298-044 (Disulfoton); S-5-methoxy-4-oxo-4H-pyran-2-ylmethyl O,O-dimethyl phosphorothioate (IUPAC), CAS Number 2778-04-3 (Endothion); O,O,O',O'-tetraethyl S,S'-methylene bis(phosphorodithioate) (IUPAC), CAS Number 563-12-2 (Ethion); O,O-dimethyl O-4-nitro-m-tolyl phosphorothioate (IUPAC); O,O-dimethyl O-(3-methyl-4-nitrophenyl)phosphorothioate (CAS), CAS Number 122-14-5 (Fenitrothion); O-ethyl S,S-dipropyl phosphorodithioate (IUPAC, CAS Number), CAS Number 13194-48-4 (Ethoprop); O,O-diethyl O-(1,2,2,2-tetrachloroethyl)phosphorothioate (CAS), CAS Number 54593-83-8 (Chlorethoxyfos); S-benzyl O,O-di-isopropyl phosphorothioate (IUPAC), CAS Number 26087-47-8 (Iprobenfos); O-5-chloro-1-isopropyl-1H-1,2,4-triazol-3-yl O,O-diethyl phosphorothioate, CAS Number 42509-80-8 (Isazofos); 1-methylethyl 2-[[ethoxy[(1-methylethyl)amino] phosphinothioyl]osy]benzoate (CAS), CAS Number 25311-71-1 (Isofenphos); O,O-Diethyl O-(5-phenyl-3-isoxazolyl) phosphorothioate (IUPAC), CAS Number 18854-01-8 (Isoxathion); O,O-dimethyl S-2-(1-methylcarbamoylethylthio)-ethyl phosphorothioate (IUPAC), CAS Number 2275-23-2 (Vamidothion); S-[2-(ethylsulfinyl)-1-methylethyl]O,O-dimethyl phosphorothioate, CAS Number 2674-91-1, (Active Ingredient of Metasystox-S) S-2,3-dihydro-5-methoxy-2-oxo-1,3,4-thiadiazol-3-ylmethyl O,O-dimethyl phosphorodithioate (IUPAC), CAS Number 950-37-8 (Methidathion); O,O-dimethyl O-(4-nitrophenyl)phosphorothioate, CAS Number 298-00-0 (Methyl Parathion); Alpha isomer of 2-carbomethoxy-1-methylvinyl dimethyl phosphate (typical 63%); Beta isomer of 2-carbomethoxy-1 methylvinyl dimethyl phosphate (typical 25%), CAS Number 7786-34-7 (Mevinphos); S-morpholinocarbonylmethyl phosphorodithioate (IUPAC), CAS Number 144-41-2, (Morphothion); 1,2-dibromo-2,2-dichloroethyl dimethyl phosphate, CAS Number 300-76-5 (Naled); Ethyl 3-methyl4-(methylthio)phenyl (1-methylethyl)-phosphoramidate (CAS), CAS Number 22224-92-6 (Fenamiphos); S-[N-(2-chlorophenyl)butyramidomethyl]O,O-dimethyl phosphordithioate (IUPAC), CAS Number 83733-82-8, (Fosmethilan); O-(1,6-dihydro-6-oxo-1-phenylpyridazin-3-yl) O,O-diethyl phosphorothioate (IUPAC), CAS Number 119-12-0 (Pyridaphenthion); O,O-dimethyl S-[2-(methylamino)-2-oxoethyl]phosphorothioate (CAS), CAS Number 1113-02-6; (Omethoate); O,O-diethyl O-(4-nitrophenyl)phosphorothioate; CAS Number 56-38-2 (Parathion); S-2,5-dichlorophenyl-thiomethyl O,O-diethyl phosphorodithioate (IUPAC), CAS Number 2275-14-1 (Phencapton); S-(α-ethyoxycarbonylbenzyl) O,O-dimethyl phosphorodithioate (IUPAC), CAS Number 2597-03-7 (Phenthoate); O,O-Diethyl S-[(ethylthio)methyl] phosphorodithioate (CAS), CAS Number 298-02-2 (Phorate); S-[(6chloro-2-oxo-3(2H)-benzoxazolyl)methyl] O,O-diethyl phosphorodithioate (CAS), CAS Number 2310-17-0 (Phosalone); S-[1,3-dihydro-1,3-dioxo-2H-isoindol-2-yl)methyl]O,O-dimethyl phosphorothioate (CAS 9CI), CAS Number 732-11-6 (Phosmet); O-4-Chloro-3-nitrophenyl O,O-dimethyl phosphorothioate (IUPAC), CAS Number 2463-84-5 (Phosnichlor); 2-chloro-2-diethylcarbamoyl-1-methylvinyl dimethyl phosphate (IUPAC), CAS Number 13171-21-6 (Phosphamidon); O-(4-bromo-2,5- dichlorophenyl) O-methyl phenylphosphonothioate, CAS Number 21609-90-5, (Leptophos); α-[[(diethoxyphosphinothioyl)oxy]imino] benzeneacetonitrile (IUPAC), CAS Number 14816-18-3 (Phoxim); O-(2-diethylamino-6-methylpyrimidin4-yl) O,O-dimethyl phosphorothioate, CAS Number 29232-93-7 (Pirimiphos-methyl); O-2-diethylamino-6-methylpyrimidin-4-yl O,O-diethyl phosphorothioate (IUPAC), Number CAS 23505-41-1 (Pirimiphos-ethyl); O-ethyl S-propyl phosphorothioate (IUPAC), CAS Number 41198-08-7 (Profenofos); S-(2,3-dihydro-5-isopropoxy-2-oxo-1,3,4-thiadiazol-3-ylmethyl) O,O-diethyl phosphorodithioate (IUPAC), CAS Number 20276-83-9 (Prothidathion); O,O-Diethyl S-(N-isopropylcarbamoylmethyl)phosphorodithioate (IUPAC), CAS Number 2275-18-5 (Prothoate); S-2-methylpiperidinocarbonylmethyl O,O-dipropyl phosphorodithioate (IUPAC); S-[2-(2-methyl-1-piperidinyl)-2-oxoethyl]O,O-dipropyl phosphorodithioate (CAS), CAS Number 24151-93-7 (Piperophos); O-(2,6-Dichloro-4-methylphenyl) O,O-dimethyl phosphorothioate (IUPAC), CAS Number 57018-04-9 (Tolclofos-methyl); O,O-Dimethyl O-(2,4,5-trichlorophenyl)phosphoro-thioate (IUPAC), CAS Number 299-84-3 (Ronnel); O-ethyl S,S-di-sec-butyl phosphorodithioate (IUPAC) or O-ethyl S,S-bis(1-methylpropyl)phosphorodithioate), FMC Corp. Code Number 67825 (Cadusafos); 5-methoxymethylcarbamolymethyl O,O-dimethyl phosphorodithioate (IUPAC), CAS Number 919-76-6 (Sophamide); Demeton, CAS Number 8065-48-3 (mixture of demeton-O (O,O-diethyl O-2-(ethylthio) ethylphosphorothioate) (IUPAC) CAS 298-03-3) and demeton-S (O,O-diethyl S-2-(ethylthio) ethylphosphorothioate) (IUPAC) CAS 126-75-0); (Demeton I (thiono isomer)) and (Demeton II (thiolo isomer)); S-[N-(1-cyano-1-methylethyl)carbamoylmethyl]O,O-diethyl phosphoro-thioate (IUPAC), CAS Number 3734-95-0 (Cyanthoate); 0-[2-(1,1-Dimethylethyl)-5-pyrimidinyl]O-ethyl O-(1-methylethyl)phosphorothioate (CAS), CAS Number 96182-53-5 (Tebupirimfos); S-[[1,1-Dimethylethyl)thio]methyl]O,O-diethyl phosphorodithioate (CAS), CAS Number 13071-79-9 (Terbufos); (Z)-2-chloro-1-(2,4,5-trichlorophenyl)vinyl dimethyl phosphate (IUPAC), CAS Number 22248-79-9 (Tetra Chlorvinphos); S-[2-(ethylthio)ethyl]O,O-dimethyl phosphoro-dithioate (CAS 8 and 9 CI), CAS Number 640-15-3 (Thiometon); O-(2,4-dichlorophenyl) O-ethyl S-propyl phosphodithioate (CAS), CAS Number 34643-46-4 (Prothiofos); S-2-Chloro-1-phthalimidoethyl O,O-diethyl phophorodithioate, CAS Number 10311-84-9 (Dialifos); Dimethyl (2,2,2-trichloro-1-hydroxyethyl)phosphonate (CAS), CAS Number 52-68-6 (Trichlorfon).

The preferred organophosphorus insecticides are chlorpyrifos, parathion, ethyl-methyl parathion, methyl parathion, dimethoate, azinphosmethyl, acephate, diazinon, malathion, ethion, and fonofos. The more preferred of these organophosphorus insecticides are chlorpyrifos, parathion, ethyl-methyl parathion, methyl parathion, dimethoate, azinphosmethyl, acephate, diazinon and malathion. The most preferred organophosphorus compounds are chlorpyrifos, oxydementon-methyl, dimethoate, methyl parathion, azinphosmethyl, parathion, ethyl-methyl parathion and certain combinations of these.

The concentration of insecticidal compound in the insecticidal composition of the present invention will depend on the specific insecticide used and the specific adjuvant composition. Generally, the insecticidal compound will be present at between about 0.015 % and about 3.6 % of the composition as applied to the substrate, e.g., plant. More preferably, the insecticidal compound will be present at between about 0.015% about 1.8% of the composition as applied to the substrate.

The Adjuvant Composition of the Present Invention

Adjuvant compositions useful in the practice of the present invention include those based on methylated seed oils such as described in U.S. Pat. Nos. 4,834,908; 5,102,442 and 5,238,604, which are incorporated herein by reference in their entirety for the adjuvants described therein. Representative preferred adjuvants are described in U.S. Pat. No. 4,834,908 as a mixture of:

(a) an anionic surfactant derived from esterification of a polyoxyalkylene nonionic surfactant with a dihydric or trihydric inorganic acid or by carboxylation with an organic acid derivative;

(b) (i) a long chain carboxylic acid and/or (ii) lower alkanol ester thereof; and (c) a hydrocarbon.

The anionic surfactants of (a) are preferably the partial sulfate and phosphate esters of polyoxyalkylene ethers. These partial esters are prepared by methods well known to those skilled in the art, for example, by reacting on of the well known and commercially available monohydric polyoxyalkylene ethers with sulfuric acid or phosphoric acid or their chemical equivalents. The sulfate esters so obtained consist predominantly of the half ester (monoester) while the phosphate esters generally contain both mono- and diesters. Also useful, are the carboxylate surfactants, as are also the simple salts of these surfactants, for example the alkali metal, alkaline earth metal or ammonium salts, particularly the latter. The preferred nonionic, monofunctional ethers used to prepare the esters are available commercially. The preferred ethers have molecular weights of from about 400 to about 3000 Daltons, more preferably, from about 600 to about 1200 Daltons. An exemplary anionic surfactant is KLEARFAC® AA-270, a phosphate ester product of BASF Corporation, Mt. Olive, N.J.

The long chain carboxylic acid component (b) (i) may have a chain length of from 10 to 22 carbon atoms. Preferably, the carboxylic acid component is selected from the group of naturally occurring fatty aids such as stearic acid, linoleic acid, palmitic acid, oleic acid and the like and mixtures thereof. The unsaturated fatty acids are preferred. The long chain carboxylic acid ester component (b) (ii) may be considered as derived from a lower alkanol having from 1 to 4 carbon atoms, such as methyl alcohol, ethyl alcohol, propyl alcohol or butyl alcohol and a long chain carboxylic acid. The methyl and ethyl esters are preferred. Most particularly, the methyl esters are utilized. The long chain carboxylic acid generally contains from 10–22 carbon atoms, preferably from 14–18 carbon atoms. Preferred are those carboxylic acids obtainable form natural sources such as fats and oils, for example, lauric, myristic, stearic, linoleic, linolenic, palmitic and oleic acids. Mixtures of these acids are also useful. Preferred are methyl esters of oleic and palmitic acids.

The hydrocarbon component (c) may be derived principally from vegetable or petroleum sources. Hydrocarbon components derived from petroleum sources may be predominately aliphatic or aromatic. Preferred are the aromatic solvents particularly those containing alkylated benzenes and naphthalenes.

The adjuvants generally contain, in percent by weight relative to the total weight of the adjuvant, from about 2 to about 30 percent anionic surfactant (a); from about 1 to about 20 percent fatty acid (b) (i) or from 10 to about 96 percent lower alkanol ester (b) (ii); and from about 90 to about 10 percent hydrocarbon component (c). More preferably, the adjuvant contains from about 2 to about 10 percent anionic surfactant (a); from about 4 to about 10 percent fatty acid (b) (i) or form 10 to about 50 percent lower alkanol ester (b) (ii); and from about 88 to about 40 percent hydrocarbon component (c). The hydrocarbon component is optional when the (b) component is a fatty acid ester.

A representative adjuvant product, as described in U.S. Pat. No. 4,834,908, is:

(a) 22.5% Klearfac® AA270 (phosphate ester anionic surfactant derived from nonionic polyether having a molecular weight of about 800 Daltons.);

(b) 37.5% C65 methylester (lower alkanol ester of a fatty acid having 4–22 carbon atoms which is approximately a 1:1 blend of methyloleate and methylpalmitate derived from natural sources) (available from Stepan Chemical Co.);

(c) 5% oleic acid (carboxylic acid);

(d) 35% aromatic® 150 solvent (mixed aromatic solvent) (available from Exxon Chemical Corporation).

One particularly preferred series of adjuvants was available from BASF Corporation, Mt. Olive, N.J. under the DASH® family of adjuvants.

The final concentration of adjuvant applied will depend upon the specific application (crop, pest, etc.) as well as the activity of the insecticide but it will typically be in the range of about 0.5 to about 99.5%. Preferably, the amount of adjuvant will be about 0.25% to about 7% of the spray mix. More preferably, the amount of adjuvant will be about 0.25% to about 4.0% of the spray mix. Most preferably, the amount of adjuvant will be about 0.25 to about 1.0% of the spray mix. It is contemplated that the adjuvant can make up as high as 99% of the applied mixture when a highly concentrated insecticidal compound is used, such as in ultra low volume application in which the adjuvant and carrier may be one and the same.

The adjuvant is typically applied at a rate of from about 0.5 pints/acre to about 2 pints per acre, with the preferred rate being about 1 pint/acre.

Optional Ingredients Useful in the Practice of the Present Invention

Optionally, the insecticidal compositions of the present invention may be blended with a wide variety of other agricultural adjuvants, diluents or carriers, including, but not limited to orgainc solvents, petroleum distillates, water or other liquid carriers, surface active dispersing agents, finely divided inert solids, etc.

Also, tank mixes may bemade of the insecticidal composition of the present invention with other herbicides, fungicides, plant growth regulators, plant nutrients, and other crop protection and/or crop management chemicals.

The Utility of the Present Invention

The composition of the present invention is useful for controlling economically important pests, including but not limited to: Corn rootworm, wireworm, flea beetle, chafer, cutworm, corn borer, fruit fly, wheat bulb fly, symphylid, mite, alfalfa weevil, aphid, leafhopper, peach twig borer, codling moth, plum curculio, leaf roller, scale, corn earworm, termite, armyworm, bollworm, budworm, boll weevil, looper, lygus, whitefly, thrip, pear psylla, Mexican bean beetle, Colorado potato beetle, greenbug, sorghum shoofly, leafminer, corn rootworm, psyllid, Hessian fly, foliar nematode, billbug, seed corn maggot, seed corn beetle, white grub and other soil insects, mealybug, mosquitoe, psyllids, cabbageworm, grape moth, spittlebug, and hornworm. The composition of the present invention is most preferably used to control pests of the lepidopteran order such as beet armyworm (*Spodoptera exigua*), tobacco budworm (*Heliothis virescens*), fall armyworm (*S. fruqiperda*), cabbage looper (*Trichoplusia ni*), diamondback moth (*Plutella aylostella*), imported cabbageworm (*Pieris rapae*) and soybean loopers (*Pseudoplusia includens*).

The insecticidal composition of the present invention can be applied to crops, including but not limited to bush and vine crops, vegetables, ornamentals, stone fruits, deciduous fruits, forage crops, cereals, citrus, legumes, etc. Exemplary specific crops are mushrooms, avocados, artichokes, asparagus, apples, apricots, almonds, beans, beets, bananas, broccoli, corn, cabbage, caneberries, cranberries, cantaloupes, cauliflower, cherries, coffee, collards, cotton, cucumbers, dewberries, eggplant, grapes, kiwifruit, lettuce, melons, mint, mustard, nectarines, peas, potatoes, peaches, pears, peppers, radishes, squash, strawberries, tea, tomatoes, turf, watermelons, and walnuts. The invention is preferably used to control pests on cotton, okra, green beans, sweet corn, soybeans and potatoes.

Preparation of the Insecticidal Composition of the Present Invention

The insecticidal composition of the present invention is prepared by blending the adjuvant with the insecticide compound. Exemplary blending techniques are described in the following non-limiting examples: Water is typically used as a diluent in the practice of the present invention. But other diluents can be used as will be apparent to the ordinarily skilled in the art. Other suitable diluents include spray oils such as vegetable, paraffinic or mineral oils. The invention will now be described by referring to the following detailed examples. These examples are set forth by way of illustration and are not intended to be limiting in scope.

EXAMPLE 1

Control of Cotton Aphid

Test plot areas were monitored for the presence of significant naturally occurring populations of the target pest(s). At the critical pest population threshold, treatments were applied to crops using a $CO_2$ pressurized backpack sprayer. The application methods were designed to simulate commercial ground application of crop protection products that is normally carried out with spray tractors equipped with a spray tank, a pressure pump and a spray rig with nozzles.

Treatments A–D and F were applied to cotton at the 9th-main stem node growth stage (early-to-mid season) with the sprayer calibrated to deliver 53 gallons per acre at 40 pounds per square inch pressure (PSI) through three 12 SX hollow cone nozzles. One plot (E) was left untreated as a control. Each test plot consisted of a 16-ft long row of crop and each treatment was replicated four times in a randomized complete block design. Counts on a natural infestation of cotton aphid were made 2 days after the treatments were applied by searching 5 cotton leaves per each treatment plot are presented in Table 1.

Treatments G–L and N were applied to okra at the 2–3 true leaf growth stage (seedling plants) with the sprayer calibrated to deliver 30 gallons/A at 40 PSI through one 12 SX hollow cone nozzles. One plot (M) was left untreated as a control. Each test plot consisted of a 40-ft long row of crop and each treatment was replicated four times in a randomized complete block design. Aphid counts (as above) were made 2 days after treatment by searching 20 okra leaves per each treatment plot (Table 2).

Treatments O–Q were applied to okra at the 1–2-leaf growth stage (seedling plants) using a $CO_2$ pressurized backpack sprayer calibrated to deliver 36 gallons/A at 40 PSI through two 12 SX hollow cone drop nozzles, one nozzle on each side of the plant. One plot (R) was left untreated as a control. Each test plot consisted of a 30-ft long row of crop, and each treatment was replicated four times in a randomized complete block design. Aphid counts (as above) were made 2 and 6 days after treatment by searching 50 plants per each treatment plot. The results of cotton aphid control can be seen in the Table 2.

A. Methyl Parathion at Half Rate Per Acre

Methyl parathion (Penncap-M™) was applied at a rate of 0.50 pounds (lb.) of active ingredient (ai) per acre (A). This is half the maximum recommended label rate for aphid control. The insecticide was combined with water at a rate of 53 gallons of water/A for delivery in the field. The ratio of the insecticides (0.50 lb. ai=8.0 ounces ai) and the water (53 gallons=7,077 ounces by weight) resulted in an insecticide concentration of 0.11%.

B. Methyl Parathion at Half Rate Per Acre Plus Adjuvant

A mixture as in A was prepared, except that the adjuvant DASH® was added to the insecticide mix at a rate of 1 quart ai/A. With the 53 gallons of water used to deliver the mix the resultant adjuvant concentration was 0.47% (1 quart=33.4 ounces divided by 7,077 ounces in 53 gallons=0.47%).

C. Oxydemeton-methyl at Full Rate Per Acre

Oxydemeton-methyl (Metasystox-R™) was used at a rate of 0.25 lb. ai/A (full recommended rate for aphid control). The insecticide was combined with water at a rate of 53 gallons of water per acre for delivery in the field. The ratio of the insecticide (0.25 lb. ai=4.0 ounces ai) and the water (53 gallons=7,077 ounces by weight) resulted in an insecticide concentration of 0.056%.

D. Oxydemeton-methyl at Full Rate Per Acre Plus Adjuvant

A Mixture as in C was used, except that the adjuvant DASH® was added to the insecticide mix at a rate of 1 quart ai/A. That rate of adjuvant mixed with the 53 gallons of water used to deliver the mix resulted in an adjuvant concentration of 0.47% (1 quart=33.4 ounces divided by 7,077 ounces in 53 gallons=0.47%).

E. Control

An untreated plot for comparison of aphid control.

F. Adjuvant Alone

The adjuvant DASH® was mixed with the 53 gallons of water used to deliver the mix resulted in an adjuvant concentration of 0.47% (1 quart 33.4 ounces divided by 7,077 ounces in 53 gallons=0.47%).

G. Methyl Parathion at Half Rate Per Acre

Methyl parathion was used at a rate of 0.50 pounds lb. ai/A (half the maximum recommended rate for aphid control). The insecticide was combined with water at a rate of 30 gallons of water per acre fordelivery in the field. The ratio of the insecticide (0.50 lb. ai=8.0 ounces ai) and the water (30 gallons=4,006 ounces by weight) resulted in an insecticide concentration of 0.20%.

H. Methyl Parathion at Half Rate Per Acre Plus Adjuvant

A mixture as in G was used except that the adjuvant DASH® was added to the insecticide mix at a rate of 1 quart of ai/A. That rate of adjuvant.mixed with the 30 gallons of water used to deliver the mix resulted in an adjuvant concentration of 0.83% (1 quart=33.4 ounces divided by 4,006 ounces in 30 gallons=0.83%).

I. Dimethoate at Full Rate Per Acre

Dimethoate (Dimate™) was used at a rate of 0.25 lb. ai/) (full recommended rate for aphid control). The insecticide mixture was combined with water at a rate of 30 gallons of water per acre for delivery in the field. The ratio of the insecticides (0.25 lb. ai=4.0 ounces ai) and the water (30 gallons=4,006 ounces by weight) resulted in an insecticide concentration of 0.10%.

J. Dimethoate at Full Rate Per Acre Plus Adjuvant

A mixture as in I was used except that the adjuvant DASH® was added to the insecticide mix at a rate of 1 quart of active ingredient per acre. That rate of adjuvant mixed with the 30 gallons of water used to deliver the mix resulted in an adjuvant concentration of 0.83% (1 quart=33.4 ounces divided by 4,006 ounces in 30 gallons=0.83%).

K. Insecticidal Combination at Full Combined Rate Per Acre

A mixture of chlorpyrifos (Lorsban™) and dimethoate was used at a rate of 0.17 and 0.14 pounds lb. ai/A, respectively, for a total of 0.31 lb. ai/A (represents about half the recommended rate for aphid control of each active ingredient, but a full rate for the combined active ingredients). The insecticide mixture was combined with water at a rate of 30 gallons of water/A for delivery in the field. The ratio of the insecticides (0.31 lb. ai=5.0 ounces ai) and the water (30 gallons=4006 ounces by weight) resulted in an insecticide concentration of 0.125%.

L. Insecticidal Combination at Full Combined Rate Per Acre Plus Adjuvant

A mixture as in K was used except that the adjuvant DASH® was added to the insecticide mix at a rate of 1 quart of ai/A. That rate of adjuvant mixed with the 30 gallons of water used to deliver the mix resulted in an adjuvant concentration of 0.83% (1 quart=33.4 ounces divided by 4,006 ounces in 30 gallons=0.83%).

M. Control

An untreated plot for comparison of aphid control.

N. Adjuvant Alone

The adjuvant DASH® was mixed with the 30 gallons of water used to deliver the mix resulted in an adjuvant concentration of 0.83% (1 quart=33.4 ounces divided by 4,006 ounces in 30 gallons=0.83%).

O. Mixture of Chlorpyrifos and Dimethoate at Full Rate

A mixture of chlorpyrifos and dimethoate was used at a rate of 0.37 and 0.67 pounds lb. ai/A, respectively, for a total of 0.67 lb. ai/A. The insecticide mixture was combined with water at a rate of 36 gallons of water/A for delivery in the field. The ratio of the insecticides (0.67 lb. ai=10.72 ounces ai) and the water (36 gallons=4807 ounces by weight) resulted in an insecticide concentration of 0.223%.

P. Mixture O Plus Adjuvant

A mixture as in O was used except that the adjuvant DASH® was added to the insecticide mix at a rate of 1 quart of ai/A. That rate of adjuvant mixed with the 36 gallons of water used to deliver the mix resulted in an adjuvant concentration of 0.69% (1 quart=33.4 ounces divided by 4807 ounces in 36 gallons=0.69%).

Q. Mixture at Reduced Rate Per Acre Plus Adjuvant

A mixture as in O was used except that DASH® adjuvant was added at 0.69% (as in B) to the insecticide mix, and the insecticide rates were lowered to 0.18 lb. ai/A of chlorpyrifos and 0.15 lb. ai/A of dimethoate for a total of 0.33 lb. ai/A and final insecticide concentration of 0.11% (5.28 ounces of insecticide divided by 4807 ounces of water).

R. Control

An untreated plot for comparison of aphid control.

cotton aphid, even at less than the maximum recommended application rate, as compared to the same insecticides alone.

TABLE 1

Cotton aphid control in cotton

| Treatment | Rate of active Ingredient (lb./A) | Water volume used to deliver (gallons/A) | Concentration of the insecticide mix | Concentration of Adjuvant in the tankmix | Cotton aphid count 2 days after treatment (% control) |
|---|---|---|---|---|---|
| E. Untreated control | — | — | — | | 1277 |
| A. Methyl parathion | 0.5 | 53 | 0.11% | | 293 (77) |
| B. Methyl parathion + Dash® | 0.5 2.0 | 53 | 0.11% | 0.47% | 86 (93) |
| C. Oxydemeton-methyl | 0.25 | 53 | 0.056% | | 74 (94) |
| D. Oxydemeton-methyl + Dash® | 0.25 2.0 | 53 | 0.056% | 0.47% | 38 (97) |
| F. Dash® | 2.0 | 53 | | 0.47% | 905 (29) |

*percent control appears in parenthesis

TABLE 2

Cotton aphid control in okra

| Treatment | Rate of active ingredient (lb./A) | Water volume used to deliver the insecticide mix (gallons/A) | Concentration of the insecticide mix | Concentration of Adjuvant in the tankmix | Cotton aphid count 2 days after treatment (% control)* | Cotton aphid count 6 days after treatment (% control)* |
|---|---|---|---|---|---|---|
| M. Untreated control | — | — | — | — | 132 | |
| G. Methyl parathion | 0.5 | 30 | 0.2% | | 21 (84) | |
| H. Methyl parathion + Dash | 0.5 2.0 | 30 | 0.2% | 0.83% | 8 (94) | |
| I. Dimethoate | 0.25 | 30 | 0.10% | | 19 (86) | |
| J. Dimethoate + Dash | 0.25 2.0 | 30 | 0.10% | 0.83% | 11 (92) | |
| K. Chlorpyrifos + Dimethoate | 0.17 0.14 0.31 | 30 | 0.125% | | 9 (93) | |
| L. Chlorpyrifos + Dimethoate + Dash | 0.17 0.14 0.31 2.0 | 30 | 0.125% | 0.83% | 4 (97) | |
| N. Dash | 2.0 | 30 | | 0.83% | 98 (26) | |
| R. Untreated control | — | — | — | | 229 | 156 |
| O. Chlorpyrifos + Dimethoate | 0.37 0.30 0.67 | 36 | 0.223% | | 69 (70) | 14 (91) |
| P. Chlorpyrifos + Dimethoate + Dash | 0.37 0.30 0.67 2.0 | 36 | 0.223% | 0.69% | 32 (86) | 26 (83) |
| Q. Chlorpyrifos + Dimethoate + Dash | 0.18 0.15 0.33 2.0 | 36 | 0.11% | 0.69% | 77 (66) | 47 (70) |

*percent control appears in parenthesis

As demonstrated by the above data, cotton aphid control by methyl parathion and a tank mix of chlorpyrifos and dimethoate at rates below the recommended maximum rate for aphid control was much higher when tank-mixed with the adjuvant than when applied alone, at the application rates tested. Improvement in aphid control was observed by tank-mixing oxydemeton-methyl, dimethoate and blends of dimethoate with chlorpyrifos at the full rate with the adjuvant. These results indicate that the use of the adjuvant in combination with certain organophosphate insecticides increases the efficacy of control of these insecticides against

EXAMPLE 2

Control of Whiteflies

Test plot areas were monitored for the presence of significant naturally occurring populations of the target pest(s). At the critical pest population threshold, treatments were applied to crops using a $CO_2$ pressurized backpack sprayer. The application methods were designed to simulate commercial ground application of crop protection products that is normally carried out with spray tractors equipped with a spray tank, a pressure pump and a spray rig with nozzles.

Treatments A–D were applied to green beans at the fruiting growth stage with the sprayer calibrated to deliver 75 gallons per acre at 40 pounds per square inch pressure (PSI) through 12 SX hollow cone nozzles. One plot (E) was left untreated as a control. Each test plot consisted of a 10-ft long row of crop and each treatment was replicated four times in a randomized complete block design. A natural infestation of whitefly adults was counted 1 and 3 days after treatment by searching 10 leaves per each treatment plot. To determine control over immatures, 3 plants were shaken so that adults flew away. The shaken plants were then covered with abag. At 7 days after treatment, the plants were cut down and frozen. The adults inside the bags were brushed onto a petri dish and counted. The whitefly counts are presented in Table 3.

Treatments F–I were applied to green beans at the 3–4$^{th}$ leaf growth stage with the sprayer calibrated to deliver 36 gallons per acre at 40 pounds per square inch pressure (PSI) through 12 SX hollow cone nozzles. One plot (J) was left untreated as a control. Each test plot consisted of a 20-ft long row of crop and each treatment was replicated four times in a randomized complete block design. Whitefly counts were made 1, 3 and 7 days after treatment by searching 18 leaves per each treatment plot. The whitefly counts are presented in Table 3.

Treatments K–M were applied to green beans at the 3–4$^{th}$ leaf growth stage with the sprayer calibrated to deliver 36 gallons per acre at 40 pounds per square inch pressure (PSI) through 12 SX hollow cone nozzles. One plot (N) was left untreated as a control. Each test plot consisted of a 20-ft long row of crop and each treatment was replicated four times in a randomized complete block design. Whitefly counts were made 1 and 3 days after treatment by searching 18 leaves per each treatment plot. The trial was terminated after the third day due to cold and rainy weather. The whitefly counts are presented in Table 3.

Control

An untreated plot for comparison of aphid control.

B. Chlorpyrifos and Dimethoate

A mixture of chlorpyrifos and dimethoate were used at a rate of 0.50 and 0.38 pounds lb. ai/A, respectively, for a total of 0.88 lb. ai/A. The tankmix rate of 0.88 lb ai represents the minimum labeled rate for whitefly control for each active ingredients. The insecticide mixture was combined with water at a rate of 36 gallons of water/A for delivery in the field. The ratio of the insecticides (0.88 lb. ai=14 ounces ai) and the water (36 gallons=4,806 ounces by weight) resulted in an insecticide concentration of 0.29%.

C. Chlorpyrifos and Dimethoate Plus Adjuvant

A mixture as in G was prepared, except that the adjuvant DASH® was added to the insecticide mix at a rate of 1 quart ai/A. With the 36 gallons of water used to deliver the mix the resultant adjuvant concentration was 0.69% (1 quart=33.4 ounces divided by 4,806 ounces in 36 gallons=0.69%).

D. Acephate

Acephate (Orthene® 90 S) was applied at a rate of 0.50 pounds (lb.) of active ingredient (ai) per acre (A). The 0.50 lb ai rate represents the minimum labeled rate of acephate for whitefly control. The insecticide was combined with water at a rate of 36 gallons of water/A for delivery in the field. The ratio of the insecticides (0.50 lb=8 ounces ai) and the water (36 gallons=4,806 ounces by weight) resulted in an insecticide concentration of 0.16%.

E. Acephate Plus Adjuvant

A mixture as in I was prepared, except that the adjuvant DASH® was added to the insecticide mix at a rate of 1 quart ai/A. With the 36 gallons of water used to deliver the mix the resultant adjuvant concentration was 0.69% (1 quart=33.4 ounces divided by 4,806 ounces in 36 gallons=0.69%).

F. Control

An untreated plot for comparison.

G. Chlorpyrifos and Dimethoate at Half Rate Per Acre

A mixture of chlorpyrifos and dimethoate were used at a rate of 0.25 and 0.20 pounds lb. ai/A, respectively, for a total of 0.45 lb. ai/A. The tankmix rate of 0.45 lb ai represents half of the minimum labeled rate for whitefly control for each active ingredients. The insecticide mixture was combined with water at a rate of 36 gallons of water/A for delivery in the field. The ratio of the insecticides (0.45 lb. ai=7.2 ounces ai) and the water (36 gallons=4,806 ounces by weight) resulted in an insecticide concentration of 0.15%.

H. Chlorpyrifos and Dimethoate Plus Adjuvant

A mixture as in G was prepared, except that the adjuvant DASH® was added to the insecticide mix at a rate of 1 quart ai/A. With the 36 gallons of water used to deliver the mix the resultant adjuvant concentration was 0.69% (1 quart=33.4 ounces divided by 4,806 ounces in 36 gallons=0.69%).

I. Acephate

Acephate (Orthene® 90 S) was applied at a rate of 1.0 pound (lb.) of active ingredient (ai) per acre (A). The 1.0 lb ai rate of acephate represents the full (maximum) recommended rate for whitefly control. The insecticide was combined with water at a rate of 36 gallons of water/A for delivery in the field. The ratio of the insecticides (1 lb=16 ounces ai) and the water (36 gallons=4,806 ounces by weight) resulted in an insecticide concentration of 0.33%.

J. Control

An untreated plot for comparison.

TABLE 3

Control of Bandedwinged Whitefly in Green Beans

| | Treatment | Rate of active ingredient (lb./A) | Water volume used to deliver the insecticide mix (gallons/A) | Concentration of the insecticide in the tankmix | Concentration of adjuvant in the tankmix | # Whitefly adults counted (% control) Days After Treatment: 1 | 3 | 7 |
|---|---|---|---|---|---|---|---|---|
| A. | Untreated check | — | | | | 637 | 1077 | 2821 |
| B. | Untreated check | — | | | | 610 | 582 | 527 |
| C. | chlorpyrifos + Dimethoate | 0.88 | 36 | 0.29% | | 174 (71) | 61 (89) | 1137 (0) |
| D. | chlorpyrifos + Dimethoate + Dash ® | 0.88 + 2.0 | 36 | 0.29% | 0.69% | 36 (94) | 62 (89) | 250 (53) |
| E. | Acephate | 0.50 | 36 | 0.16% | | 24 (96) | 10 (98) | 54 (90) |

TABLE 3-continued

Control of Bandedwinged Whitefly in Green Beans

| Treatment | | Rate of active ingredient (lb./A) | Water volume used to deliver the insecticide mix (gallons/A) | Concentration of the insecticide in the tankmix | Concentration of adjuvant in the tankmix | # Whitefly adults counted (% control) Days After Treatment: | | |
|---|---|---|---|---|---|---|---|---|
| | | | | | | 1 | 3 | 7 |
| F. | Acephate + Dash ® | 0.50 + 2.0 | 36 | 0.16% | ).69% | 18 (97) | 10 (98) | 99 (81) |
| N. | Check | — | | | | 472 | 462 | |
| K. | chlorpyrifos + Dimethoate | 0.45 | 36 | 0.15% | | 69 (85) | 52 (89) | |
| L. | Chlorpyrifos + Dimethoate + Dash ® | 0.45 + 2.0 | 36 | 0.15% | 0.69% | 25 (95) | 32 (93) | |
| M. | Acephate | 1.0 | 36 | 030% | | 11 (98) | 8 (98) | |

These data show that the addition of the adjuvant to tankmixes of chlorpyrifos +dimethoate at the minimum labeled rate or half the minimum labeled rate for whitefly control resulted in better knockdown and residual control of bandedwinged whitefly as compared to the insecticide tankmix at the same rates alone. Furthermore, the above insecticides plus Dash had comparable control to acephate at the full rate, but were weaker than acephate when applied alone. These results indicate that the use of Dash can result in a reduction of the rates needed for effective whitefly control by the organophosphate insecticides chlorpyrifos and dimethoate.

EXAMPLE 3

Control of Lepidopterous Pests

Test plot areas were monitored for the presence of significant naturally occurring populations of the target pest(s). At the critical pest population threshold, treatments were applied to crops using a $CO_2$ pressurized backpack sprayer. The application methods were designed to simulate commercial ground application of crop protection products that is normally carried out with spray tractors equipped with a spray tank, a pressure pump and a spray rig with nozzles.

Treatments A–D were applied to cotton at the fruiting growth stage with the sprayer calibrated to deliver 20 gallons per acre at 40 pounds per square inch pressure (PSI) through 12 SX hollow cone nozzles. One plot (E) was left untreated as a control. Each test plot consisted of a 30-ft long row of crop and each treatment was replicated four times in a randomized complete block design. Beet armyworm population was counted on a 13-ft row section of the plot by using a drop cloth. To assess control of tobacco budworm, the number of damaged bolls in 50 bolls from a 10 square meter plot were counted. The counts were made 3 days after the treatment. The average counts are presented in Table 4.

Treatments F–J were applied to sweet corn at the 1–2 leaf growth stage with the sprayer calibrated to deliver 33 gallons per acre at 40 pounds per square inch pressure (PSI) through 12 SX hollow cone nozzles. One plot (K) was left untreated as a control. Each test plot consisted of a 20-ft long row of crop and each treatment was replicated four times in a randomized complete block design. Beet armyworm and fall armyworm populations were counted on a 13-ft row section of the plot 4 days after treatment. The average counts are presented in Table 5.

Treatments L and M were applied to soybeans at the fruiting growth stage with the sprayer calibrated to deliver 20 gallons per acre at 40 pounds per square inch pressure (PSI) through 12 SX hollow cone nozzles. One plot (N) was left untreated as a control. Each test plot consisted of 2–10 ft long rows of crop and each treatment was replicated four times in a randomized complete block design. Soybean looper populations were counted on a 4 meter square section of each plot 3 days after treatment. The trial was terminated thereafter due to cold rainy weather. The average counts are presented in Table 6.

A. Chlorlpyrifos and Dimethoate

A mixture of chlorpyrifos and dimethoate were used at a rate of 0.37 and 0.25 pounds lb. ai/A, respectively, for a total of 0.621 lb. ai/A. The rate of chlorpyrifos used is half the minimum recommended rate for beet armyworm control, whereas dimethoate is not labeled for beet armyworm control. The insecticide mixture was combined with water at a rate of 20 gallons of water/A for delivery in the field. The ratio of the insecticides (0.62 lb=9.9 ounces ai) and the water (20 gallons=2,670 ounces by weight) resulted in an insecticide concentration of 0.37%.

B. Chlorpyrifos and Dimethoate Plus Adjuvant

A mixture as in A was prepared, except that the adjuvant DASH® was added to the insecticide mix at a rate of 1 quart ai/A. With the 20 gallons of water used to deliver the mix the resultant adjuvant concentration was 1.25% (1 quart=33.4 ounces divided by 2,670 ounces in 20 gallons=1.25%).

C. Chlorpyrifos

Chlorpyrifos was applied at a rate of 0.50 pounds (lb.) of active ingredient (ai) per acre (A). This rate of chlorpyrifos is two-thirds the lowest recommended rate for beet armyworm control. The insecticide was combined with water at a rate of 20 gallons of water/A for delivery in the field. The ratio of the insecticides (0.50 lb=8 ounces ai) and the water (20 gallons=2,670 ounces by weight) resulted in an insecticide concentration of 0.30%.

D. Chlorpyrifos Plus Adjuvant

A mixture as in C was prepared, except that the adjuvant DASH® was added to the insecticide mix at a rate of 1 quart ai/A. With the 20 gallons of water used to deliver the mix the resultant adjuvant concentration was 1.25% (1 quart=33.4 ounces divided by 2,670 ounces in 20 gallons=1.25%).

E. Control

An untreated plot for comparison.

F. Chlorpyrifos and Dimethoate

A mixture of chlorpyrifos and dimethoate were used at a rate of 0.25 and 0.20 pounds lb. ai/A, respectively, for a total of 0.45 lb. ai/A. The rate of chlorpyrifos used is one-third the minimum recommended rate for beet armyworm control, and half the minimum recommended rate for fall armyworm control, whereas dimethoate is not labeled for beet armyworm or fall armyworm control. The insecticide mixture was combined with water at a rate of 33 gallons of water/A for delivery in the field. The ratio of the insecticides (0.45 lb. ai=7.2 ounces ai) and the water (33 gallons=4,405 ounces by weight) resulted in an insecticide concentration of 0.16%.

G. Chlorpyrifos and Dimethoate Plus Adjuvant

A mixture as in F was prepared, except that the adjuvant DASH® was added to the insecticide mix at a rate of 1 quart ai/A. With the 33 gallons of water used to deliver the mix the resultant adjuvant concentration was 0.76% (1 quart=33.4 ounces divided by 4,405 ounces in 33 gallons=0.76%).

H. Chlorpyrifos

Chlorpyrifos was applied at a rate of 0.94 pounds (lb.) of active ingredient (ai) per acre (A). This rate of chlorpyrifos is the maximum recommended rate for beet and fall armyworm control. The insecticide was combined with water at a rate of 33 gallons of water/A for delivery in the field. The ratio of the insecticides (0.94 lb=15 ounces ai) and the water (33 gallons=4,405 ounces by weight) resulted in an insecticide concentration of 0.34%.

I. Chlornyrifos Plus Adjuvant

A mixture as in H was prepared, except that the adjuvant DASH® was added to the insecticide mix at a rate of 1 quart ai/A. With the 33 gallons of water used to deliver the mix the resultant adjuvant concentration was 0.76% (1 quart=33.4 ounces divided by 4,405 ounces in 33 gallons=0.76%).

J. Adjuvant Alone

The adjuvant DASH® was mixed with the 33 gallons of water used to deliver the mix resulted in an adjuvant concentration of 0.76% (1 quart=33.4 ounces divided by 4,405 ounces in 33 gallons=0.76%).

K. Control

An untreated plot for comparison.

L. Chlorpyrifos and Dimethoate

A mixture of chlorpyrifos and dimethoate were used at a rate of 0.25 and 0.20 pounds lb. ai/A, respectively, for a total of 0.45 lb. ai/A. The insecticide mixture was combined with water at a rate of 20 gallons of water/A for delivery in the field. The ratio of the insecticides (0.45 lb. ai=7.2 ounces ai) and the water (20 gallons=2,670 ounces by weight) resulted in an insecticide concentration of 0.27%.

M. Chlorpyrifos and Dimethoate Plus Adjuvant

A mixture as in L was prepared, except that the adjuvant DASH® was added to the insecticide mix at a rate of 1 quart ai/A. With the 20 gallons of water used to deliver the mix the resultant adjuvant concentration was 1.25% (1 quart=33.4 ounces divided by 2,670 ounces in 20 gallons=1.25%).

N. Control

An untreated plot for comparison of lepidopteran count.

TABLE 4

Control of Beet Armyworm in Cotton and Tobacco Budworm in Cotton

| Treatment | Rate of active ingredient (lb./A) | Water volume used to deliver (gallons/A) | Concentration of the insecticide in the tankmix | Concentration of Adjuvant in the tankmix | # Beet Armyworms (% control) 3 days after treatment | % Bolls Damaged by Tobacco Budworm 3 DAT |
|---|---|---|---|---|---|---|
| E. Control | — | | | | 112 | 45 |
| A. Chlorpyrifos + Dimethoate | 0.62 | 20 | 0.37% | | 92 (18) | 45 |
| B. Chlorpyrifos + Dimethoate + Dash ® | 0.62 + 2.0 | 20 | 0.37% | 1.25% | 21 (81) | 47 |
| C. Chlorpyrifos | 0.50 | 20 | 0.30% | | 73 (38) | 42 |
| D. Chlorpyrifos + Dash ® | 0.50 + 2.0 | 20 | 0.30% | 1.25% | 42 (76) | 44 |

TABLE 5

Control of Beet Armyworm and Fall Armyworm in Sweet Corn

| Insecticide | Rate of active ingredient (lb./A) | Water volume used to deliver (gallons/A) | Concentration of the insecticide mix | Concentration of Adjuvant in the tankmix | # Beet Armyworm (% control) 4 DAT | # Fall Armyworm (% control) 4 DAT |
|---|---|---|---|---|---|---|
| K. Control | — | | | | 3 | 5 |
| F. Chlorpyrifos + Dimethoate | 0.45 | 33 | 0.16% | | 3 (0) | 0.50 (90) |
| G. Chlorpyrifos + Dimethoate + Dash ® | 0.45 + 2.0 | 33 | 0.16% | 0.76% | 2 (33) | 0 (100) |
| H. Chlorpyrifos | 0.94 | 33 | 0.34% | | 1 (66) | 0.25 (95) |
| I. Chlorpyrifos + Dash ® | 0.94 + 2.0 | 33 | 0.34% | 0.76% | 1 (66) | 0.25 (95) |
| J. Dash ® | 2.0 | 33 | | 0.76% | 6 (0) | 2 (60) |

These results show that chlorpyrifos at half-to-two-thirds the labeled rate for beet armyworm control provided effective and better beet armyworm control when takmixed with Dash than when applied alone at the same rates. A similar trend was observed on the more susceptible fall armyworm.

TABLE 6

Control of Soybean Looper in Soybeans

| Treatment | Rate of active ingredient (lb./A) | Water volume used to deliver (gallons/A) | Concentration of the insecticide in the tankmix | Concentration of Adjuvant in the tankmix | # Soybean Loopers 3 DAT |
|---|---|---|---|---|---|
| N. Control | — | | | | 10 ± 2 |
| L. Chlorpyrifos + Dimethoate | 0.45 | 20 | 0.27% | | 12 ± 5 |
| M. Chlorpyrifos + Dimethoate + Dash ® | 0.45 + 2.0 | 20 | 0.27% | 1.25% | 11 ± 2 |

EXAMPLE 4

Control of Thrips in Cotton

Treatments were applied to crops using a $CO_2$ pressurized backpack sprayer. The application methods were designed to simulate commercial ground application of crop protection products that is normally carried out with spray tractors equipped with a spray tank, a pressure pump and a spray rig with nozzles.

Treatments A–F were applied to cotton at the 2–3$^{rd}$ true leaf growth stage (seedling plants) with the sprayer calibrated to deliver 15 gallons per acre at 40 pounds per square inch pressure (PSI) through two 12 SX hollow cone nozzles. One plot (A) was left untreated as a control. Each test plot consisted of a 65-ft long row of crop and each treatment was replicated four times in a randomized complete block design. Thrips were counted 1–9 days after treatment by collecting 10 cotton plants from each test plot at random, the plants were washed with a water and detergent+bleach solution in the laboratory. The water was then poured onto a coffee filter and from there thrips were rinsed onto a filter paper to be counted under a scope. The data are presented in Table 7.

A. Untreated Control

An untreated plot for comparison of control.

B. Acephate at Full Rate Per Acre

Acephate (Orthene™) was applied at a rate of 0.20 pounds (lb.) of active ingredient (ai) per acre (A). This is the maximum recommended label rate for thrips control. The insecticide was combined with water at a rate of 15 gallons of water/A for delivery in the field. The ratio of the insecticides (0.20 lb. ai=3.2 ounces ai) and the water (15 gallons=2,003 ounces by weight) resulted in an insecticide concentration of 0.16%.

C. Acephate at Full Rate Per Acre Plus Adjuvant

A mixture as in B was prepared, except that the adjuvant DASH® was added to the insecticide mix at a rate of 1 quart ai/A. With the 15 gallons of water used to deliver the mix the resultant adjuvant concentration was 1.67% (1 quart=33.4 ounces divided by 2,003 ounces in 15 gallons=1.67%).

D. Dicrotophos at Full Rate Per Acre

Dicrotophos (Bidrin™) was used at a rate of 0.20 lb. ai/A (full recommended rate for thrips control). The insecticide was combined with water at a rate of 15 gallons of water per acre for delivery in the field. The ratio of the insecticide (0.20 lb. ai=3.2 ounces ai) and the water (15 gallons=2,003 ounces by weight) resulted in an insecticide concentration of 0.16%.

E. Dicrotophos at Full Rate Per Acre Plus Adjuvant

A Mixture as in D was used, except that the adjuvant DASH® was added to the insecticide mix at a rate of 1 quart ai/A. That rate of adjuvant mixed with the 15 gallons of water used to deliver the mix resulted in an adjuvant concentration of 1.67% (1 quart=33.4 ounces divided by 2,003 ounces in 15 gallons=1.67%).

E. Adjuvant Alone

The adjuvant DASH® was mixed with the 15 gallons of water used to deliver the mix resulted in an adjuvant concentration of 1.67% (1 quart=33.4 ounces divided by 2,003 ounces in 15 gallons=1.67%).

TABLE 7

Control of Thrips in Cotton

| Insecticide | Rate of active ingredient (lb./A) | Water volume used to deliver (gallons/A) | Concentration of the insecticide mix (%) | Concentration of Adjuvant in the tankmix (%) | # Thrips/10 Plants[1] (% control) 0 DAT | 1 DAT | 5 DAT | 9 DAT |
|---|---|---|---|---|---|---|---|---|
| A. Control | — | | | | 252 ± 88 | 115 ± 50 | 65 ± 43 | 36 ± 32 |
| B. Acephate | 0.20 | 15 | 0.16% | | 174 ± 50 | 21 ± 9 (80) | 42 ± 17 (35) | 20 ± 18 (44) |
| C. Acephate + Dash | 0.20 2.0 | 15 | 0.16% | 1.67% | 164 ± 63 | 18 ± 13 (84) | 36 ± 20 (45) | 26 ± 19 (28) |
| D. Dicrotophos (Bidrin 8 EC) | 0.20 | 15 | 0.16% | | 228 ± 108 | 31 ± 12 (73) | 36 ± 28 (45) | 35 ± 16 (03) |
| E. Dicrotophos + Dash | 0.20 2.0 | 15 | 0.16% | 1.67% | 237 ± 123 | 43 ± 38 (63) | 40 ± 11 (38) | 27 ± 22 (25) |
| F. Dash | 2.0 | 15 | | 1.67% | 186 ± 31 | 68 ± 49 (41) | 66 ± 25 (00) | 52 ± 33 (00) |

EXAMPLE 5

Control of Colorado Potato Beetle

The efficacy of Guthion™ (azinphosmethyl) alone and in combination with Dash HC® against the Colorado Potato Beetle (*Leptinotarsa decemlineata*) on potatoes. The test plot area was monitored for the presence of significant naturally occurring populations of the target pest, Colorado potato beetle (CPB). At the critical pest population threshold, treatments were applied to 6 meter, single row plots of the crop using a CO2 pressurized backpack sprayer.

Treatments were sprayed on potatoes in the early bloom stage to a mature population of the Colorado potato beetle. Larvae were evaluated in two classes: class one=first and second instar larvae, class two=third and fourth instar. Population counts were taken at 3 and 7 days after treatment. Trial results can be seen in Table 8.

A. Untreated Control

An untreated plot for comparison of beetle control.

B. Azinphosmethyl at Full Rate Per Acre

Azinphosmethyl was applied at a rate of 0.375 lb ai/A. The recommended rate for CPB control. The insecticide was combined with water at a rate of 64.1 gal/acre. Gal/acre. This resulted in an insecticide concentration of 0.07%105%

C. Azinphosmethyl at 20% Reduced Rate

Azinphosmethyl was applied at a rate of 0.30 lb ai/A. This is a 20% reduction below the recommended rate for CPB control. The insecticide was combined with water at a rate of 64.1 gal/Acre. This resulted in an insecticide concentration of 0.056%.

D. Azinphosmethyl at ½ Full Rate

Azinphosmethyl was applied at a rate of 0.19 lb ai/A. This is ½ of the recommended label rate for CPB control. The insecticide was combined with water at a rate of 64.1 gal/acre. This resulted in an insecticide concentration of 0.035%.

E. Azinphosmethyl at Full Rate Plus Adjuvant

Azinphosmethyl was applied at a rate of 0.375 lb ai/A. The recommended rate for CPB control. The insecticide was combined with water at a rate of 64.1 gal/a. This resulted in an insecticide concentration of 0.07% With the 64.1 gal of water used to deliver the mix, the resultant adjuvant concentration was 0.383%.

F. Azinphosmethyl at 20% Reduced Rate Plus Adjuvant

Azinphosmethyl was applied at a rate of 0.30 lb ai/A. This is a 20% reduction below the recommended rate for CPB control. The insecticide was combined with water at a rate of 64.1 gal/Acre. This resulted in an insecticide concentration of 0.056%. With the 64.1 gal of water used to deliver the mix, the resultant adjuvant concentration was 0.383%.

G. Azinphosmethyl at ½ Full Rate Plus Adjuvant

Azinphosmethyl was applied at a rate of 0.19 lb ai/A. This is ½ of the recommended label rate for CPB control. The insecticide was combined with water at a rate of 64.1 gal/acre. This resulted in an insecticide concentration of 0.035%. With the 64.1 gal of water used to deliver the mix, the resultant adjuvant concentration was 0.383%.

As demonstrated by the above data, in 12 possible paired comparisons between insecticide performance with and without the adjuvant, the insecticide/adjuvant combination performed better in 8 comparisons (67% of the time). Equivalent in one comparison (8%)., and worse than the insecticide alone in 3 comparisons (25%).

EXAMPLE 6

Control of Cabbage Pests

The efficacy of chlorpyrifos plus Dash® adjuvant against the cabbage pests: cabbage looper (*Trichoplasia ni*), diamondback moth (*Plutella xylostelia*), and imported cabbageworm (*Pieris rapae*) is assessed in this example.

The test plot area was monitored for the presence of significant naturally occurring populations of the target pests. At the critical pest population threshold, treatments were applied to 6 meter, single row plots of the crop using a CO2 pressurized backpack sprayer. The trial was sprayed with a 3-nozzle boom: one tip positioned over the center of the row, two tips on drops on either side of the row. Spray volume was 43 gal/acre. The cabbage was just beginning to head at application. Each treatment had 3 replicates. Total larvae of each species were counted from 3 plants per plot, on 4 and 7 DAT. Data were statistically analyzed using the SQRT (X+0.5) transformation. The results are presented in Table 9.

A. Untreated Control

An untreated plot for comparison of control.

B. Chlorpyrifos at Full Rate Per Acre

Chlorpyrifos was applied at a rate of 1.24 lb ai/A, the recommended label rate. The insecticide was combined with water at 43 gal/acre. This resulted in an insecticide concentration of 0.35%.

C. Chlorpyrifos at 20% Reduced Rate (80% of Label Rate)

Chlorpyrifos was applied at a rate of 1.0 lb ai/A, a 20% reduction of the recommended label rate. The insecticide was combined with water at 43 gal/acre. This resulted in an insecticide concentration of 0.28%.

D. Chlorpyrifos at ½ Label Rate

Chlorpyrifos was applied at a rate of 0.62 lb ai/A, a 50% reduction of the recommended label rate. The insecticide was combined with water at 43 gal/acre. This resulted in an insecticide concentration of 0.173%.

E. Chlorpyrifos at Full Rate Plus Adjuvant

Chlorpyrifos was applied at a rate of 1.24 lb ai/A, the recommended label rate. The insecticide was combined with water at 43 gal/acre. This resulted in an insecticide concen-

TABLE 8

Control of Colorado Potato Beetle in Potatoes

| Treatment | Rate of active ingredient lb ai/A. | Total Number of larvae from a six meter plot | | | |
|---|---|---|---|---|---|
| | | 3 DAT L2 | 3 DAT L4 | 7 DAT L2 | 7 DAT L4 |
| A. Control | — | 29.7 | 79.3 | 3.0 | 24.3 |
| B. azinphosmethyl | 0.375 lb ai/A | 0.7 | 12.3 | 6.0 | 5.0 |
| C. azinphosmethyl | 0.30 lb ai/a | 5.0 | 7.7 | 1.0 | 3.0 |
| D. azinphosmethyl | 0.19 lb ai/A | 4.0 | 11.7 | 1.3 | 6.0 |
| E. azinphosmethyl + adjuvant | 0.375 lb ai/A (0.88 lb/A) | 5.3 | 1.7 | 3.3 | 9.0 |
| F. azinphosmethyl + adjuvant | 0.30 lb ai/A + (0.88 lb/A) | 5.0 | 8.0 | 0.3 | 1.3 |
| G. azinphosmethyl + adjuvant | 0.19 lb ai/A + (0.88 lb/A) | 1.7 | 6.3 | 1.0 | 5.0 | tration of 0.35%. With the 43 gal of water used to deliver the mix, the resultant adjuvant concentration was 0.26%.

F. Chlorpyrifos at 80% Label Rate Plus Adjuvant

Chlorpyrifos was applied at a rate of 1.0 lb ai/A, a 20% reduction of the recommended label rate. The insecticide was combined with water at 43 gal/acre. This resulted in an insecticide concentration of 0.28%. With the 43 gal of water used to deliver the mix, the resultant adjuvant concentration was 0.26%.

G. Chlorpyrifos at ½ Label Rate Plus Adjuvant

Chlorpyrifos was applied at a rate of 0.62 lb ai/A, a 50% reduction of the recommended label rate. The insecticide was combined with water at 43 gal/acre. This resulted in an insecticide concentration of 0.173%. With the 43 gal of water used to deliver the mix, the resultant adjuvant concentration was 0.26%.

TABLE 9

Control of Cabbage Pests in Cabbage

| | | # of larvae | | | | | |
|---|---|---|---|---|---|---|---|
| | Rate | 4DAT | | | 7DAT | | |
| Treatment | (lb.ai/A) | TRIPNI | PLUTMA | PIERRA | TRIPNI | PLUTMA | PIERRA |
| A. Control | — | 1.7 | 2.3 | 4.7 | 0.3 | 1.7 | 2.3 |
| B. Chlorpyrifos | 1.24 | 0.7 | 1.0 | 0 | 0.7 | 1.0 | 1.3 |
| C. Chlorpyrifos | 1.0 | 1.3 | 0.3 | 0 | 2.0 | 0 | 1.0 |
| D. Chlorpyrifos | 0.62 | 2.7 | 0.7 | 0 | 0.7 | 0.3 | 0.3 |
| E. Chlorpyrifos | 1.24 0.88 lb/a | 2.0 | 0.7 | 0.7 | 1.3 | 0.3 | 3.0 |
| F. Chlorpyrifos + DASH ®* | 1.0 0.88 lb/a | 3.0 | 0.3 | 0 | 1.0 | 0.3 | 1.0 |
| G. Chlorpyrifos + DASH ®* | 0.62 0.88 lb/a | 3.0 | 5.0 | 4.0 | 0.7 | 0.7 | 2.7 |

EXAMPLE 7
Airblast Application

An air blast sprayer utilizes a fan or pump to create a high speed air stream that transports and deposits pesticide solutions in orchard and vine crops to control sucking pests in tree fruits such as aphids, scale crawlers, lygus bug, pear psylla, peach twig borer and leafhoppers.

The addition of the adjuvant DASH improves the performance of chlorpyrifos by enhancing coverage on both target pests and foliage. The organophosphate insecticide chlorpyrifos is applied at a rate of 0.25 lb. ai/100 gallons of water/A. DASH adjuvant is included at the rate of 4 pints per 100 gallons. The rate range of chlorpyrifos is from 0.25–0.5 lb. ai/100 gallons.

Treatments are applied with conventional air blast spray rigs to control sucking pests. This method is representative of a commercial ground application of crop protection products utilized in tree fruits.

EXAMPLE 8
Aerial Application of Organophospate Insecticide

The organophosphate insecticide profenofos (Curacron™) is aerially applied at 1.0 lb. ai/A in combination with DASH adjuvant at 2 pints per acre. The insecticide is combined with water at 3–10 gallons. The volume of water/A is determined by crop growth stage and application equipment. The concentration of active ingredient rate of profenofos when sprayed at the above water volumes would be 1.2–4.0%. The addition of adjuvant improves the performance of profenofos by enhancing coverage on both target pests and foliage. The concentration of the adjuvant Dash when sprayed at the above water volumes would be 2.4–8.0%.

Treatments are aerially applied to control lepidopterous pests such as armyworms and Helicoverpa spp. This application method is representative of commercial aerial applications of crop protection products utilized in cotton.

EXAMPLE 9
Ultra Low Volume Aerial Application

Area-wide control of migratory locusts in Northern Africa and the Middle East, as well as control of mosquitoes, which vector malaria, yellow fever, and other tropical diseases, requires widespread ultra low volume (ULV) aerial sprays of less than one gallon per acre. In such applications, the adjuvant is combined with malathion, chlorpyrifos, or another insecticide, with no additional water, other carriers, or additives. Malathion is used at a rate of 0.5 lb. ai/and is mixed with DASH adjuvant with no additional water, other carriers or additives. The adjuvant-malathion mix is applied at a volume of 1.0 gallon/A, and is delivered in the field using an aerial ULV sprayer. The concentration of malathion and adjuvant is 6% for malathion and 94% for adjuvant.

This type of ULV application is common in the tropics where the area to be treated is extensive, and the ground is rugged. The addition of DASH improves the performance of malathion (and other insecticides) by enhancing coverage on both target pests and the surfaces on which they alight.

What is claimed is:

1. A method for controlling insect populations of the lepidopteran order in crops comprising:

applying to said crop to control said populations an effective amount of an insecticidal composition comprising:
from about 0.015% to about 3.6% of one or more organophosphate insecticidal compounds;
from about 0.5% to about 99.5% of an adjuvant composition comprising, based on the weight of the adjuvant:
from about 20 to about 90 weight percent of a lower alkanol ester of a fatty acid containing from 4–22 carbon atoms;
from about 4 to about 40 weight percent of an anionic surfactent selected from the group consisting of partial sulfate and phosphate esters and carboxlates of monohydroxylfunctional polyoxyalkylene ethers;
from about 2 to about 20 weight percent of a long chain carboxylic acid containing from about 10 to about 20 carbon atoms; and optionally, a hydrocarbon component; and diluent.

2. The method of claim 1 wherein said organophosphate is selected from the group consisting of:

acephate; formothion azamethiphos; azinphos-ethyl; azinphos-methyl; chlorfenvinphos; cyanophos; danifos; fensulfothion; tribifos; O,O-diethyl O-[6-methyl-2(1-methylethyl)-4-pyrimidinyl]phosphorothloate; O,O-diethyl O-(2isopropyl-6-methyl-4-pyrimidinyl) phosphorothioate; dimethoate; dioxathion; disulfoton; endothion; ethion; fenitrothion; ethoprop; chlorethoxyfos; iprobenfos; isazofos; isofenphos; isoxathion; vamidothion; S-[2-(ethylsulfinyl)-1-methylethyl]O,O-dimethyl phosphorothioate; methidathion; methyl parathion; alpha isomer of 2-carbomethoxy-1-methylvinyl dimethyl phosphate; beta isomer of 2-carbomethoxy-1 methylvinyl dimethyl phosphate; morphothion; naled; fenamiphos; fosmethilan; pyridaphenthion; omethoate; parathion; phencapton; phenthoate; phorate; phosalone; phosmet; phosnichlor; phosphamidon; leptophos; phoxim; pirimiphos-methyl; pirimiphos-ethyl; profenofos; prothidathion; prothoate; piperophos; tolclofos-methyl; ronnel; cadusafos; sophamide; demeton, demeton I (thiono isomer); demeton II (thiolo isomer); cyanthoate; tebupirimfos; terbufos; tetra chlorvinphos; thiometon; prothiofos; dialifos; trichlorfon; and combinations of these.

3. The method of claim 2 wherein said organophosphate is selected from the group consisting of:

chlorpyrifos; parathion; dimethoate; azinphosmethyl; acephate; diazinon; malathion; oxydementon-methyl; ethyl parathion; methyl parathion; ethion; fonofos; and combinations of these.

4. The method of claim 3 wherein said organophosphate is selected from the group consisting of:

chlorpyrifos; oxydementon-methyl; dimethoate; methyl parathion; azinphosmethyl; parathion; ethyl parathion; methyl parathion; and combinations of these.

5. A method of controlling insect populations of the lepidopteran order in crops comprising:

applying to said crop to control said populations an effective amount of an insecticidal composition comprising:

about 0.5%–about 99.5% of an adjuvant composition comprising, based on the weight of the adjuvant:
(a) from about 30 to about 80 percent of a lower alkanol ester of a fatty acid containing from 10 to about 20 carbon atoms;
(b) from about 4 to about 20 percent of an anionic surfactant selected from the group consisting of the partial sulfate and phosphate esters and carboxylates of monohydroxyl-functional polyoxyalkylene ethers having an average molecular weight of from 600 to about 1200 Daltons; and
(c) from 4 to about 6 percent of a long chain carboxylic acid having from 10 to about 20 carbon atoms;
about 0.00075%–about 1.8% of one or more organophosphate insecticidal compounds; and
diluent.

6. The method of claim 5 wherein said organophosphate is selected from the group consisting of:

acephate; formothion; azamethiphos; azinphos-ethyl; azinphos-methyl; chlorfenvinphos; cyanophos; danifos; fensulfothion; tribifos; O,O-diethyl O-[6-methyl-2(1-methyfethyl)-4-pyrimidinyl]phosphorothioate; O,O-diethyl O-(2isopropyl-6-methyl-4-pyrimidinyl) phosphorothioate; dimethoate; dioxathion; disulfoton; endothion; ethion; fenitrothion; ethoprop; chlorethoxyfos; iprobenfos; isazofos; isofenphos; isoxathion; vamidothion; S-[2-(ethylsulfinyl)-1-methylethyl]O,O-dimethyl phosphorothioate; methidathion; methyl parathion; alpha isomer of 2-carbomethoxy-1-methylvinyl dimethyl phosphate; beta isomer of 2-carbomethoxy-1 methylvinyl dimethyl phosphate; morphothion; naled; fenamiphos; fosmethilan; pyridaphenthion; omethoate; parathion; phencapton; phenthoate; phorate; phosalone; phosmet; phosnichlor; phosphamidon; leptophos; phoxim; pirimiphos-methyl; pirimiphos-ethyl; profenofos; prothidathion; prothoate; piperophos; toiclofos-methyl; ronnel; cadusafos; sophamide; demeton, demeton I (thiono isomer); demeton II (thiolo isomer), cyanthoate; tebupirimfos; terbufos; tetra chlorvinphos; thiometon; prothiofos; dialifos; trichlorfon; and combinations of these.

7. The method of claim 6 wherein said organophosphate is selected from the group consisting of:

chlorpyrifos; parathion; dimethoate; azinphosmethyl; acephate; diazinon; malathion; oxydementon-methyl; ethyl parathion; methyl parathion; ethion; fonofos; and combinations of these.

8. The method of claim 7 wherein said organophosphate is selected from the group consisting of:

chlorpyrifos; oxydementon-methyl; dimethoate; methyl parathion; azinphosmethyl; parathion; ethyl parathion; methyl parathion; and combinations of these.

9. A method for controlling insect populations of the lepidopteran order in crops comprising:

applying to said crop to control said populations an effective amount of an insecticidal composition comprising:

about 0.5%–about 99.5% of an adjuvant composition comprising, based on the weight of the adjuvant:
(a) from about 2 to about 30 percent of an anionic surfactant selected from the group consisting of the partial sulfate and phosphate esters and carboxylates of monohydroxyl-functional polyoxyalkylene ethers and their alkali metal, alkaline earth metal and ammonium salts;
(b) one of the following fatty acid components:
(i) from 1 to about 20 percent of a fatty acid having from 10 to about 22 carbon atoms; and
(ii) from 10 to about 96 percent of a lower alkanol ester of a fatty acid having form 10 to about 22 carbon atoms; and
(c) a hydrocarbon component which is
(i) from 90 to about 10 percent when the fatty acid component is (b) (i); and
(ii) up to about 70 percent when the fatty acid component is (b) (ii);
about 0.015%–about 3.6% of one or more organophosphate insecticidal compounds selected from the group consisting of acephate; formothion; azamethiphos; azinphos-ethyl; azinphos-methyl; chlorfenvinphos; cyanophos; danifos; fensulfothion; tribufos; O,O-diethyl O-[6-methyl-2(1-methylethyl)-4-pyrimidinyl]phosphorothioate; O,O-diethyl O-(2isopropyl-6-methyl-4-pyrimidinyl) phosphorothioate; dimethoate; dioxathion; disulfoton; endothion; ethion; fenitrothion; ethoprop; chlorethoxyfos; iprobenfos; isazofos; isofenphos; isoxathion; vamidothion; S-[2-(ethylsulfinyl)-1-methylethyl]O,O-dimethyl phosphorothioate; methidathion; methyl parathion; alpha isomer of 2-carbomethoxy-1-methylvinyl dimethyl phosphate; beta isomer of 2-carbomethoxy-1 methylvinyl dimethyl phosphate; morphothion; naled; fenamiphos; fosmethilan; pyridaphenthion; omethoate; parathion; phencapton; phenthoate; phorate; phosalone; phosmet; phosnichlor; phosphamidon; leptophos; phoxim; pirimiphos-methyl; pirimiphos-ethyl; profenofos; prothidathion; prothoate; piperophos; toiclofos-methyl; ronnel; cadusafos; sophamide; demeton, demeton I (thiono isomer); demeton II (thiolo isomer); cyanthoate; tebupirimfos; terbufos; tetra chlorvinphos; thiometon; prothiofos; dialifos; trichlorfon; and combinations of these; and diluent.

10. The method of claim 9 wherein said organophosphate is selected from the group consisting of:

acephate; formothion; azamethiphos; azinphos-ethyl; azinphos-methyl; chlorfenvinphos; cyanophos; danifos; fensulfothion; tribufos; O,O-diethyl O-[6-methyl-2(1-methylethyl)-4-pyrimidinyl]phosphorothioate; O,O-diethyl O-(2isopropyl-6-methyl-4-pyrimidinyl) phosphorothioate, dimethoate; dioxathion, disulfoton; endothion; ethion; fenitrothion; ethoprop; chlorethoxyfos; iprobenfos; isazofos; isofenphos; isoxation; vamidothion; S-[2-(ethylsulfinyl)-1-methylethyl]O,O-dimethyl phosphorothioate; methidathion; methyl parathion; alpha isomer of 2-carbomethoxy-1-methylvinyl dimethyl phosphate; beta isomer of 2-carbomethoxy-1 methylvinyl dimethyl phosphate; morphothion; naled: fenamiphos; fosmethilan; pyridaphenthion; omethoate; parathion; phencapton; phenthoate; phorate; phosalone; phosmet; phosnichlor, phosphamidon; leptophos; phoxim; pirimiphos-methyl; pirimiphos-ethyl; profenofos; prothidathion; prothoate; piperophos; toiclofos-methyl; ronnel; cadusafos; sophamide; demeton, demeton I (thiono isomer); demeton II (thiolo isomer); cyanthoate; tebupirimfos; terbufos; tetra chlorvinphos; thiometon; prothiofos; dialifos; trichlorfon; and combinations of these.

11. The method of claim 10 wherein said organophosphate is selected from the group consisting of:

chlorpyrifos; parathion; dimethoate; azinphosmethyl; acephate; diazinon; malathion; oxydementon-methyl; ethyl parathion; methyl parathion; ethion; fonofos; and combinations of these.

12. The method of claim 11 wherein said organophosphate is selected from the group consisting of:

chlorpyrifos; oxydementon-methyl; dimethoate; methyl parathion; azinphosmethyl; parathion; ethyl parathion; methyl parathion; and combinations of these.

* * * * *